US012759021B2

(12) United States Patent
Kim et al.

(10) Patent No.: US 12,759,021 B2
(45) Date of Patent: Oct. 13, 2026

(54) ULTRASONIC WAVE GENERATING APPARATUS CAPABLE OF ADJUSTING FOCUSING DEPTH OF ULTRASONIC WAVES

(71) Applicant: JEISYS MEDICAL INC., Seoul (KR)

(72) Inventors: Kyuntae Kim, Seoul (KR); Won Ju Yi, Seoul (KR); Dong Hwan Kang, Seoul (KR)

(73) Assignee: JEISYS MEDICAL INC., Seoul (KR)

( * ) Notice: Subject to any disclaimer, the term of this patent is extended or adjusted under 35 U.S.C. 154(b) by 243 days.

(21) Appl. No.: 18/502,391

(22) Filed: Nov. 6, 2023

(65) Prior Publication Data

US 2024/0066555 A1 Feb. 29, 2024

Related U.S. Application Data

(63) Continuation of application No. PCT/KR2022/006020, filed on Apr. 27, 2022.

(30) Foreign Application Priority Data

May 13, 2021 (KR) ........................ 10-2021-0061981

(51) Int. Cl.
*B06B 3/00* (2006.01)
*A61N 7/02* (2006.01)

(52) U.S. Cl.
CPC . *B06B 3/00* (2013.01); *A61N 7/02* (2013.01)

(58) Field of Classification Search
CPC .................................... B06B 3/00; A61N 7/02
See application file for complete search history.

(56) References Cited

U.S. PATENT DOCUMENTS 10,856,842 B2 12/2020 Park et al.
2015/0321026 A1* 11/2015 Branson .................. A61N 7/00 601/2

(Continued)

FOREIGN PATENT DOCUMENTS

JP 2018-500075 A 1/2018
JP 2018-525104 A 9/2018

(Continued)

OTHER PUBLICATIONS

European Search Report regarding Application No. 22807670.9, Aug. 21, 2024.

(Continued)

*Primary Examiner* — Keith M Raymond
*Assistant Examiner* — Ashish S. Jasani

(57) ABSTRACT

Disclosed is an ultrasonic wave generating apparatus capable of adjusting a focus depth of ultrasonic waves including a handpiece, a cartridge housing separably mounted on the handpiece, an ultrasonic wave generating unit provided in the cartridge housing and including a transducer that generates ultrasonic waves, a movable shaft that is movable in an axial line direction and a vertical direction of the transducer, and a guide part provided in the cartridge housing, and that guides the ultrasonic wave generating unit such that the ultrasonic wave generating unit is movable in the vertical direction and an axial line direction of the movable shaft. The guide part includes a guide shaft passing through the ultrasonic wave generating unit.

12 Claims, 5 Drawing Sheets

(56) References Cited

U.S. PATENT DOCUMENTS

| | | | |
|---|---|---|---|
| 2016/0001097 A1 | 1/2016 | Cho et al. | |
| 2016/0017561 A1 | 1/2016 | Lindholm et al. | |
| 2017/0303895 A1 | 10/2017 | Park et al. | |
| 2018/0236270 A1 | 8/2018 | Hananel et al. | |
| 2019/0366129 A1 | 12/2019 | Park et al. | |
| 2021/0387023 A1 | 12/2021 | Kim et al. | |

FOREIGN PATENT DOCUMENTS

| | | | | | |
|---|---|---|---|---|---|
| JP | 2020505116 | A | | 2/2020 | |
| JP | 2021194537 | A | | 12/2021 | |
| KR | 10-2012-0040909 | A | | 4/2012 | |
| KR | 20120040909 | A | * | 4/2012 | ............... A61N 7/02 |
| KR | 10-1335476 | B1 | | 12/2013 | |
| KR | 20140009052 | A | * | 1/2014 | ............ C08G 64/34 |
| KR | 10-2014-0067482 | A | | 6/2014 | |
| KR | 20150115432 | A | * | 10/2015 | ............ A61H 23/02 |
| KR | 10-2017-0074716 | A | | 6/2017 | |
| KR | 20170095549 | A | * | 8/2017 | ............... A61N 7/02 |
| KR | 10-2018-0015095 | A | | 2/2018 | |
| KR | 20180015095 | A | * | 2/2018 | ............... A61N 7/02 |
| KR | 10-2117636 | B1 | | 6/2020 | |

OTHER PUBLICATIONS

Japanese Patent Office, Notice of Reasons for Refusal regarding JP Application No. 2024-503777, Dec. 16, 2024.

International Preliminary Report on Patentability received for PCT application No. PCT/KR2022/006020, mailed on Nov. 23, 2023, 9 pages (6 pages of English Translation and 3 pages of Original Document).

International Search Report issued in PCT/KR2022/006020; mailed Aug. 3, 2022.

Office Action issued in KR 10-2021-0061981; mailed by the Korean Intellectual Property Office on Jan. 27, 2023.

* cited by examiner

ULTRASONIC WAVE GENERATING APPARATUS CAPABLE OF ADJUSTING FOCUSING DEPTH OF ULTRASONIC WAVES

CROSS-REFERENCE TO RELATED APPLICATIONS

The present application is a continuation of International Patent Application No. PCT/KR2022/006020, filed on Apr. 27, 2022, which is based upon and claims the benefit of priority to Korean Patent Application No. 10-2021-0061981 filed on May 13, 2021. The disclosures of the above-listed applications are hereby incorporated by reference herein in their entirety.

BACKGROUND

Embodiments of the inventive concept described herein relate to an ultrasonic wave generating apparatus for adjusting a focus depth of ultrasonic waves, which has a handpiece to generate ultrasonic waves, and a cartridge housing that is separably coupled to the handpiece.

Ultrasonic waves refer to waves having a frequency of 20 kHz or higher, and are widely used in the medical field for the diagnosis and treatment of affected areas as well as for skin care.

In particular, high intensity focused ultrasonic (HIFU) waves, which are in a form of high-intensity focused ultrasonic waves, may be non-invasively focused at a target depth in skin while not damaging a surface of the skin, unlike laser and radio frequency (RF) high-frequency waves. As a result, while a rapid temperature increase is induced at the target depth in the skin, coagulative necrosis of cells occurs without leaving side effects on various affected parts of the skin. These necrotic cells are naturally removed by the body's mechanism for repairing damaged cells.

Meanwhile, a conventional ultrasonic wave generating apparatus has a cartridge housing and an ultrasonic wave generating unit embedded in the cartridge housing to irradiate ultrasonic waves.

According to the conventional ultrasonic wave generating apparatus, because the ultrasonic wave generating unit is fixed inside the cartridge housing, it is difficult to adjust a focus depth of the ultrasonic waves of the ultrasonic wave generating unit.

In recent years, a technology for adjusting a focus depth of ultrasonic waves of an ultrasonic wave generating unit with one cartridge without replacing the cartridge by moving the ultrasonic wave generating unit has been developed, but it is difficult to uniformly irradiate ultrasonic waves according to a target depth in skin because it is difficult to maintain a horizontal state of the ultrasonic wave generating unit after the ultrasonic save generating unit is moved to a targeted focus depth.

SUMMARY

Embodiments of the inventive concept provide an ultrasonic wave generating apparatus that may easily adjust a focus depth of ultrasonic waves according to a target depth in skin.

Embodiments of the inventive concept also provide an ultrasonic wave generating apparatus that may uniformly irradiate ultrasonic waves according to a target depth in skin.

The problems to be solved by the inventive concept are not limited to the above-mentioned problems, and the unmentioned problems will be clearly understood by an ordinary person in the art from the following description.

According to an embodiment, an ultrasonic wave generating apparatus capable of adjusting a focus depth of ultrasonic waves includes a handpiece, a cartridge housing separably mounted on the handpiece, an ultrasonic wave generating unit provided in the cartridge housing and including a transducer that generates the ultrasonic waves, a movable shaft that is movable in an axial line direction and a vertical direction of the transducer, and a guide part provided in the cartridge housing, and that guides the ultrasonic wave generating unit such that the ultrasonic wave generating unit is movable in the vertical direction and an axial line direction of the movable shaft, and the guide part includes a guide shaft passing through the ultrasonic wave generating unit.

According to an embodiment, the guide part may further include one or more elastic members provided in the ultrasonic wave generating unit.

According to an embodiment, the elastic members may be disposed to face each other while the guide shaft being interposed therebetween, and elastically support the guide shaft.

According to an embodiment, the ultrasonic wave generating unit may include a mounter, to which the movable shaft is coupled to be separable, a fixing hole may be formed in any one of the movable shaft and the mounter, and a fixing boss which is separably coupled to the fixing hole may be formed on the other one of the movable shaft and the mounter.

According to an embodiment, a tapered portion, which has an inner diameter getting smaller in an insertion direction of the fixing boss, may be formed on one side of the fixing hole, into which the fixing boss is inserted.

According to an embodiment, the ultrasonic wave generating apparatus may further include a first tube and a second tube formed on opposite sides of the mounter and that is expanded and contracted.

According to an embodiment, the ultrasonic wave generating apparatus may further include a first magnetic member provided in the fixing hole, and a second magnetic member provided in the fixing boss and magnetically coupled to the first magnetic member.

According to an embodiment, an ultrasonic wave generating apparatus capable of adjusting a focus depth of ultrasonic waves includes a handpiece, a cartridge housing separably mounted on the handpiece, an ultrasonic wave generating unit provided in the cartridge housing and including a transducer that generates the ultrasonic waves, a variable shaft connected to the ultrasonic wave generating unit, that is movable in a vertical direction of the transducer, and that is expanded and contracted in an axial line direction thereof, and a manipulation part that moves the variable shaft in the vertical direction.

According to an embodiment, the ultrasonic wave generating apparatus may further include a movable shaft that is movable in the axial line direction of the variable shaft.

According to an embodiment, the ultrasonic wave generating apparatus may further include a guide part provided in the cartridge housing, and that guides the ultrasonic wave generating unit such that the ultrasonic wave generating unit is movable in the vertical direction and the axial line direction of the variable shaft, and the guide part may include a guide shaft passing through the ultrasonic wave generating unit.

According to an embodiment, the guide part may further include one or more elastic members provided in the ultrasonic wave generating unit.

According to an embodiment, the elastic members may be disposed to face each other while the guide shaft being interposed therebetween, and elastically support the guide shaft.

According to an embodiment, the variable shaft may include one or more shafts having different diameters, and being inserted and extracted in multiple steps.

Other detailed items of the inventive concept are included in the detailed description and the drawings.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
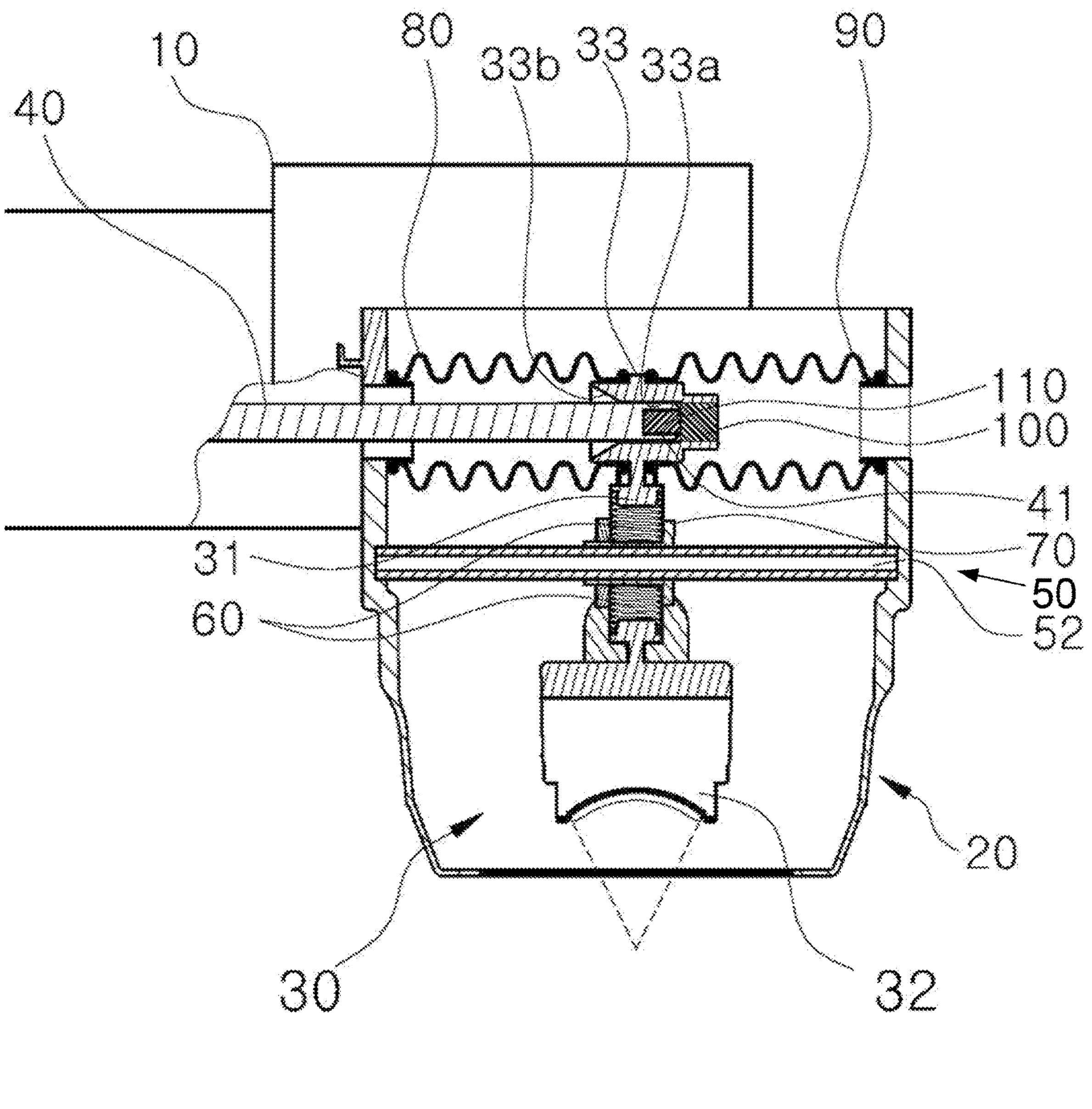
FIG. 1 is a perspective view illustrating an ultrasonic wave generating apparatus capable of adjusting a focus depth of ultrasonic waves according to an embodiment of the inventive concept.

The advantages and the features of the inventive concept, and the method for achieving them will become apparent from the following description of the embodiments, which will be described below in detail, together with the accompanying drawings. However, the inventive concept is not limited by the embodiments disclosed below and may be implemented in various different forms, and the embodiments are simply provided to make the disclosure of the inventive concept complete and to fully inform an ordinary person in the art, to which the inventive concept pertains, of the scope of the inventive concept, and the inventive concept is defined only by the scope of the claims.

The terms used in the specification is for explaining the embodiments, and are not intended to limit the inventive concept. A singular expression includes a plural expression unless an exemption is explicitly described in the context. The terms "comprises" and/or "comprising" used herein does not exclude presence or addition of one or more other elements, in addition to the aforementioned elements. Throughout the specification, the same reference numerals denote the same elements, and "and/or" includes the respective elements and all combinations of the elements. Although "first," "second" and the like are used to describe various elements, the elements are not limited by the terms. The terms are used simply to distinguish one element from other elements. Accordingly, it is apparent that a first element mentioned in the following may be a second element without departing from the spirit of the inventive concept.

Unless otherwise defined, all terms (including technical and scientific terms) used herein have the same meaning as commonly understood by those skilled in the art to which the inventive concept pertains. Furthermore, the terms defined in commonly used dictionaries should not be interpreted in an idealized or overly formal sense unless expressly so defined herein.

Hereinafter, the embodiments of the inventive concept will be described in detail with reference to the accompanying drawings.

Figure 2:
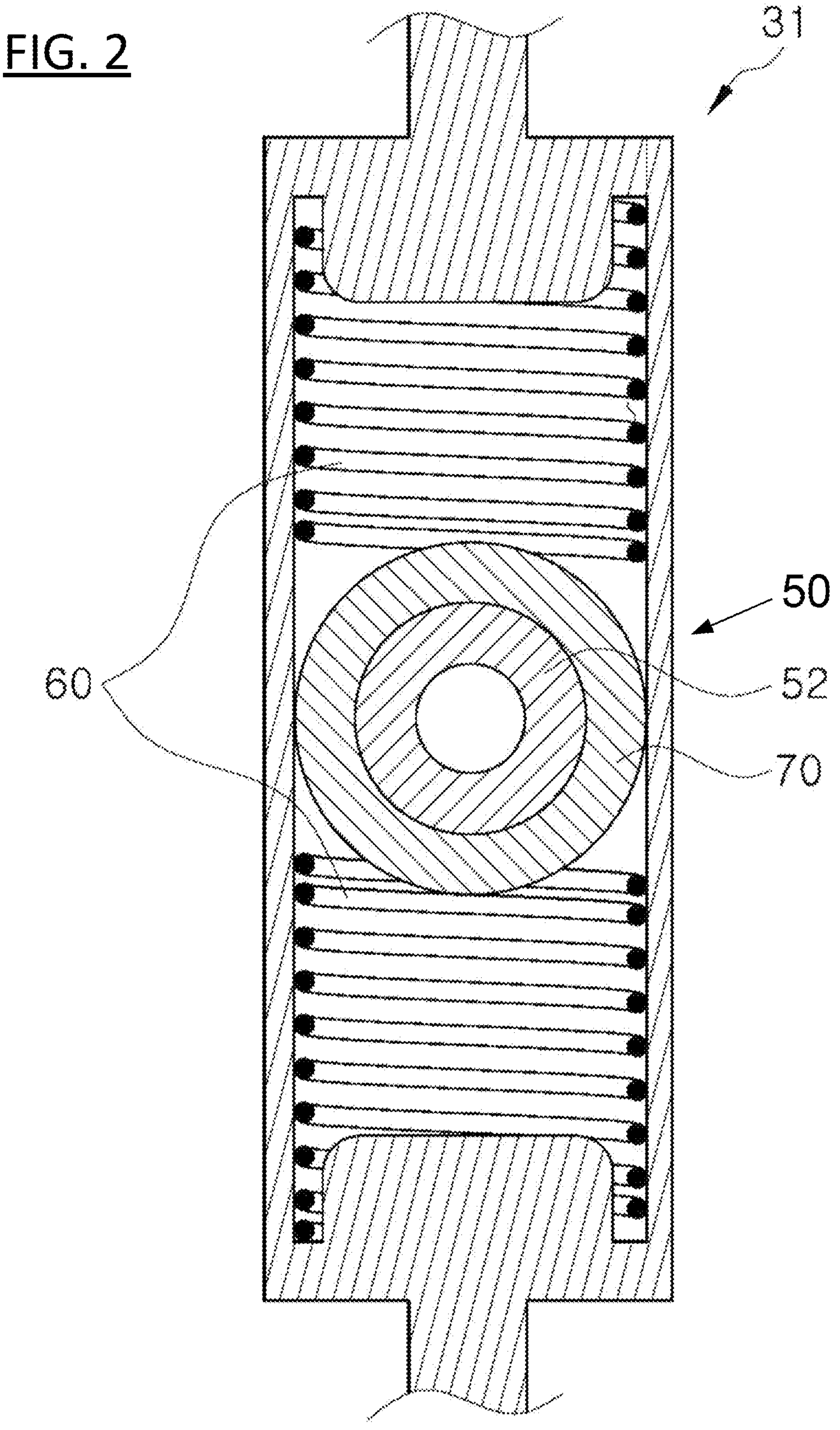
FIG. 2 is a cross-sectional view illustrating a connector of an ultrasonic wave generating apparatus capable of adjusting a focus depth of ultrasonic waves according to an embodiment of the inventive concept.

FIG. 1 is a perspective view illustrating an ultrasonic wave generating apparatus capable of adjusting a focus depth of ultrasonic waves according to an embodiment of the inventive concept, and FIG. 2 is a cross-sectional view illustrating a connector of the ultrasonic wave generating apparatus capable of adjusting a focus depth of ultrasonic waves according to an embodiment of the inventive concept.

As illustrated in FIG. 1, the ultrasonic wave generating apparatus capable of adjusting a focus depth of ultrasonic waves according to an embodiment of the inventive concept may include a handpiece 10, a cartridge housing 20, an ultrasonic wave generating unit 30, a movable shaft 40, and a guide part 50.

Here, the handpiece 10 and the cartridge housing 20 correspond to a body, the ultrasonic wave generating unit 30 functions to generate ultrasonic waves, the movable shaft 40 functions to move the ultrasonic wave generating unit 30 in a vertical direction of a transducer 32 and an axial line direction of the movable shaft 40, and the guide part 50 functions to guide the ultrasonic wave generating unit 30 such that the ultrasonic wave generating unit 30 may be moved in the vertical direction of the transducer 32 and the axial line direction of the movable shaft 40. Here, the vertical direction of the transducer 32 may be defined as a direction, in which a focus depth of ultrasonic waves of the transducer 32 is changed.

The handpiece 10 is a basic body, and may be utilized as a gripper for gripping a user, and the cartridge housing 20, which will be described below, is separably coupled to one side of the handpiece 10. The ultrasonic wave generating unit 30 that generates ultrasonic waves is disposed in an interior of the cartridge housing 20. Accordingly, in a state in which the user grips the handpiece 10 and moves the handpiece 10 such that the cartridge housing 20 gets in close contact with the surface of skin, the user irradiates the ultrasonic waves generated by the ultrasonic wave generating unit 30 to a target depth in the skin to carry out an ultrasonic medical surgery.

A cable connected to an RF board for applying an RF current to the ultrasonic wave generating unit 30 may be provided in an interior of the handpiece 10. The RF board may be accommodated in the handpiece 10, and may intermittently or continuously apply RF currents to the ultrasonic wave generating unit 30.

The cartridge housing 20 is a kind of case that accommodates the ultrasonic wave generating unit 30, and is separably coupled to the handpiece 10.

A fluid medium for delivering the ultrasonic waves generated by the ultrasonic wave generating unit 30 may be accommodated in the cartridge housing 20. Here, the fluid medium may be distilled water, degassing liquid, and silicon, but is not particularly limited thereto.

The ultrasonic wave generating unit 30 is provided in the cartridge housing 20, and includes a connector 31 and the transducer 32.

The connector 31 is provided in the cartridge housing 20, and one side of the connector 31 is connected to the movable shaft 40 and an opposite side of the connector 31 is connected to the transducer 32.

The transducer 32 may receive an electrical signal from the RF board by using the cable of the handpiece 10, and may focus the ultrasonic waves to a specific location. Here, the vertical direction of the transducer 32 may be a vertical direction with respect to the drawings. Here, a vertical distance from a distal end of the cartridge housing 20 to the specific location, at which the ultrasonic waves are focused, may be defined as a focus depth of the ultrasonic waves of the transducer 32. In the embodiment, the focus depth of the ultrasonic waves of the transducer 32 may be adjusted as the transducer 32 is moved in the vertical direction, and this will be described below.

The ultrasonic wave generating unit 30 may be separably coupled to the cartridge housing 20. For example, the ultrasonic wave generating unit 30 may be screw-coupled to the cartridge housing 20. Furthermore, the ultrasonic wave generating unit 30 may be separably coupled to the cartridge housing 20 through a boss and a recess.

The guide part 50 may include a guide shaft 52 that passes through the ultrasonic wave generating unit 30.

One or more elastic members 60 that elastically support the inserted guide shaft 52, which will be described below, may be provided in the ultrasonic wave generating unit 30.

The guide shaft 52 may be provided in the cartridge housing 20, may be inserted into the ultrasonic wave generating unit, and may guide movement of the transducer 32 in the vertical direction and movement of the movable shaft 40 in the axial line direction thereof. The guide shaft 52 may be disposed in parallel to the movable shaft 40, but the inventive concept is not particularly limited thereto.

The one or more elastic members 60 may be provided in the ultrasonic wave generating unit 30.

The one or more elastic members 60 may elastically support the guide shaft 52. In detail, a pair of elastic members 60 may be provided, and the pair of elastic members 60 may be disposed to face each other in the vertical direction while a bushing 70, on which the guide shaft 52 is slid, being interposed therebetween to elastically support the bushing 70. The elastic members 60 may be springs, but the inventive concept is not limited thereto. In this way, because the pair of elastic members 60 elastically support the ultrasonic wave generating unit 30, the ultrasonic wave generating unit 30 may be prevented from being pivoted when the ultrasonic wave generating unit 30 is moved in the vertical direction.

The bushing 70 surrounds a specific portion of the guide shaft 52. The bushing 70 may be slid in the axial line direction of the guide shaft 52, and the connector 31 also may be slid in the axial line direction of the guide shaft 52 in conjunction therewith. Meanwhile, the pair of elastic members 60 may be disposed to face each other in the vertical direction while the bushing 70 being interposed therebetween, and may elastically support the bushing 70 that is disposed in an interior of the connector 31 of the ultrasonic wave generating unit 30.

Here, in the embodiment, although the bushing 70 is coupled to the guide shaft 52 to be slid and the bushing 70 is elastically supported by the pair of elastic members 60, the inventive concept is not limited thereto and the bushing 70 may be optionally provided. In this case, the connector 31 may be moved in the axial line direction of the guide shaft 52, and the guide shaft 52 may be elastically supported by the pair of elastic members 60.

The movable shaft 40 may be coupled to the ultrasonic wave generating unit 30, and may be moved in the axial line direction and the vertical direction of the transducer 32. The movable shaft 40 may be moved by a driving device. Here, the driving device may be a forward motor, a hydraulic motor, a pneumatic motor, and an engine, but the inventive concept is not limited thereto, and any device that may supply a torque to the movable shaft 40 may be used.

Meanwhile, the ultrasonic wave generating unit 30 may include a mounter 33, to which the movable shaft 40 is coupled to be separable. In other words, the movable shaft 40 may be coupled to the mounter 33 that is provided in the connector 31 of the ultrasonic wave generating unit 30, to be separable. Accordingly, when the movable shaft 40 is moved in the vertical direction of the transducer 32 and the axial line direction of the movable shaft 40, the mounter 33 also may be moved in the vertical direction of the transducer 32 and the axial line direction of the movable shaft 40 in conjunction therewith.

Additionally, a fixing hole **33*a* is formed in any one of the movable shaft 40 and the mounter 33 and a fixing boss 41 that is coupled to the fixing hole 33*a* to be separable is formed in the other one of the movable shaft 40 and the mounter 33 whereby the movable shaft 40 and the mounter 33** may be coupled to each other to be separable.

Referring to FIG. 1, the fixing boss 41 may be formed at a distal end of the movable shaft 40, and the fixing hole **33*a* may be formed in the mounter 33. The fixing boss 41 of the movable shaft 40 may be coupled to the fixing hole 33*a* of the mounter 33 to be separable. Furthermore, the fixing boss 41 may be disposed on the same axis as that of the fixing hole 33*a***.

Meanwhile, a tapered portion **33*b*, which has an inner diameter getting smaller in an insertion direction of the fixing boss 41, may be formed on one side of the fixing hole 33*a*, into which the fixing boss 41 is inserted. Accordingly, when the fixing boss 41 is inserted into the fixing hole 33*a*, the tapered portion 33*b* may function to guide the fixing boss 41 into the fixing hole 33*a*. In addition, the tapered portion 33*b* may function to correct a location of the fixing boss 41 until the fixing boss 41** is disposed in a fixing recess on the same axis.

Additionally, the fixing boss 41 and the fixing hole **33*a* may be coupled to each other to be separable by a first magnetic member 100 and a second magnetic member 110**.

Here, the first magnetic member 100 may be provided in the fixing hole **33*a* and the second magnetic member 110 may be provided in the fixing boss 41 to be magnetically coupled to the first magnetic member 100. The first magnetic member 100 may have an opposite polarity to that of the second magnetic member 110 and the second magnetic member 110 also may have an opposite polarity to that of the first magnetic member 100 whereby the first magnetic member 100 and the second magnetic member 110** may be coupled to each other to be separable.

Meanwhile, the ultrasonic wave generating apparatus capable of adjusting a focus depth of ultrasonic waves according to an embodiment of the inventive concept may further include a first tube 80 and a second tube 90 that are provided on opposite sides of the mounter 33 to be expanded and contracted according to the axial line direction of the movable shaft 40.

The first tube 80 may be disposed to surround the movable shaft 40, and one end of the first tube 80 may be supported by one surface of the cartridge housing 20 and an opposite end of the first tube 80 may be pressed against one side of the mounter 33. A sealing member may be installed on a contact surface of the first tube 80 and the mounter 33, and the sealing member may function to ensure a sealing performance to prevent a fluid medium from penetrating into the first tube 80.

One end of the second tube 90 may be pressed against an opposite side of the mounter 33, and an opposite end of the second tube 90 may be supported by an opposite surface of the cartridge housing 20. The sealing member may be installed on a contact surface of the second tube 90 and the mounter 33, and the sealing member may function to ensure a sealing performance to prevent a fluid medium from penetrating into the second tube 90.

Cross-sections of the first tube 80 and the second tube 90 have a circular or elliptical shape, but the inventive concept is not particularly limited thereto.

In detail, the elliptical tubes may have a form that the length in the vertical direction of the transducer 32 is longer than that in other directions. Because the first tube 80 and the second tube 90 are formed to be elliptical in this way, a movement range of the movable shaft 40 may be ensured and a sealing performance between an interior and an exterior of the cartridge housing 20 may be ensured as well when the movable shaft 40 is moved in the vertical direction of the transducer 32.

Furthermore, because the first tube 80 and the second tube 90 may be formed of a material, such as urethane or silicon, which has soft characteristics, a higher reliability of sealing performance may be ensured, for example, by restraining a possibility of generation of an aperture in the first tube 80 and the second tube 90 to prevent leakage of the medium.

Hereinafter, an example of adjusting a focus depth of ultrasonic waves of the transducer 32 of the ultrasonic wave generating apparatus according to a first embodiment of the inventive concept will be described.

Figure 3:
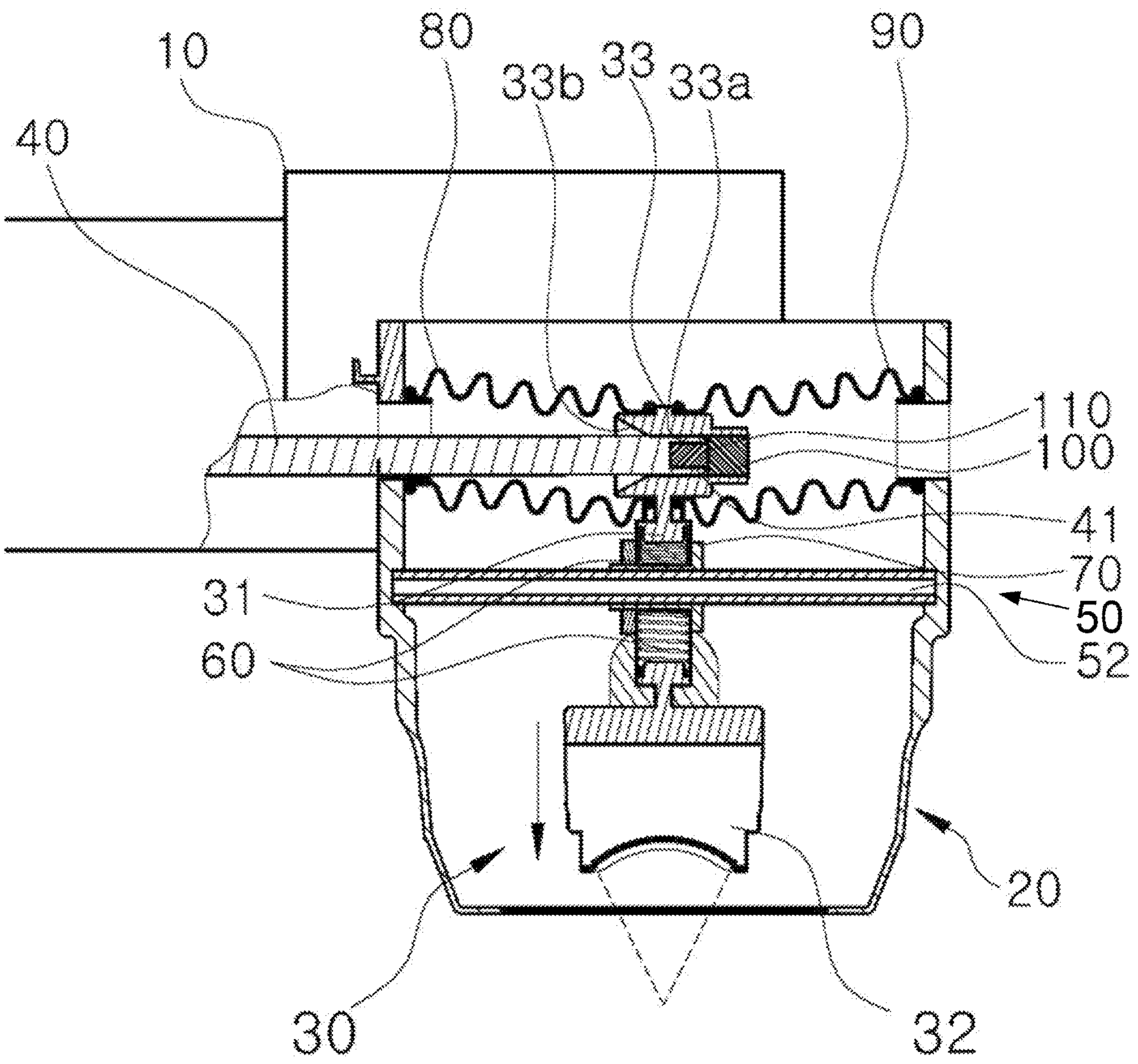
FIGS. 3 and 4 are operation views illustrating states, in which a focus depth of ultrasonic waves of a transducer of an ultrasonic wave generating apparatus according to a first embodiment of the inventive concept is adjusted.
Figure 4:
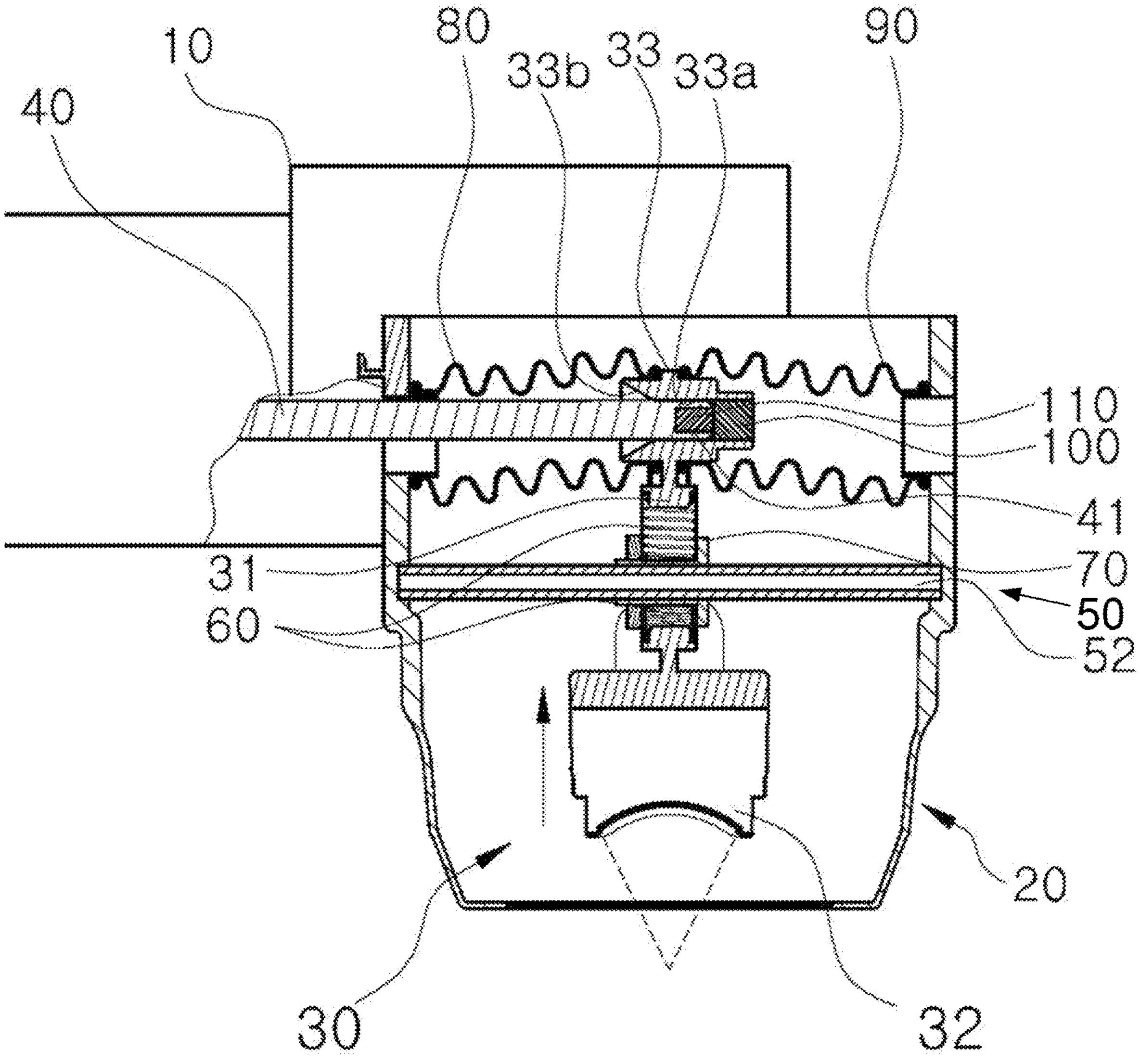

FIGS. 3 and 4 are operation views illustrating states, in which a focus depth of ultrasonic waves of the transducer of the ultrasonic wave generating apparatus according to the first embodiment of the inventive concept is adjusted.

As illustrated in FIG. 3, first, a driving device moves the movable shaft 40 downwards. Of course, the movable shaft 40 may be manually moved downwards through a manipulation by the user.

Next, the ultrasonic wave generating unit 30 also is moved downwards in conjunction with downward movement of the movable shaft 40. As a result, the focus depth of the ultrasonic waves of the transducer 32 increases.

Then, while the ultrasonic wave generating unit 30 is moved in the vertical direction of the transducer 32, the pair of elastic members 60 may elastically support the ultrasonic wave generating unit 30 to prevent the ultrasonic wave generating unit 30 from being pivoted.

Subsequently, as illustrated in FIG. 4, the driving device moves the movable shaft 40 upwards. Of course, the movable shaft 40 may be manually moved upwards through a manipulation by the user.

Next, the ultrasonic wave generating unit 30 also is moved upwards in conjunction with upward movement of the movable shaft. As a result, the focus depth of the ultrasonic waves of the transducer 32 decreases.

Then, while the ultrasonic wave generating unit 30 is moved in the vertical direction of the transducer 32, the pair of elastic members 60 elastically support the ultrasonic wave generating unit 30 to prevent the ultrasonic wave generating unit 30 from being pivoted.

Figure 5:
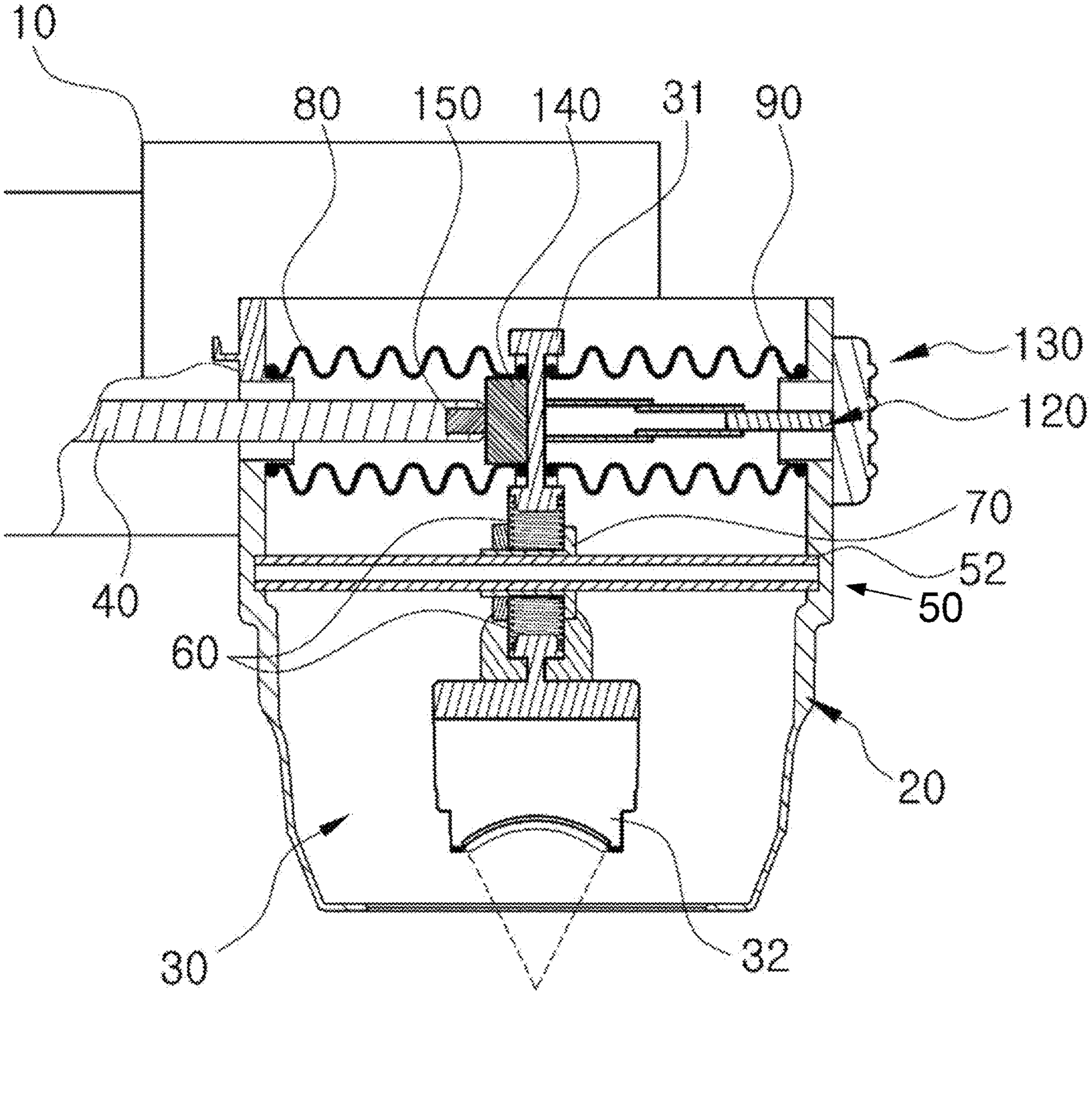
FIG. 5 is a perspective view illustrating an ultrasonic wave generating apparatus capable of adjusting a focus depth of ultrasonic waves according to another embodiment of the inventive concept.

FIG. 5 is a perspective view illustrating an ultrasonic wave generating apparatus capable of adjusting a focus depth of ultrasonic waves according to another embodiment of the inventive concept.

As illustrated in FIG. 5, unlike the one embodiment of the inventive concept, the ultrasonic wave generating apparatus capable of adjusting a focus depth of ultrasonic waves according to another embodiment of the inventive concept further includes a variable shaft 120 and a manipulation part 130. Furthermore, in the embodiment, the first magnetic member 100 and the second magnetic member 110 may be replaced by a third magnetic member 140 and a fourth magnetic member 150.

The variable shaft 120 is connected to the ultrasonic wave generating unit 30, is provided to be movable in the vertical direction of the transducer 32, and may be expanded and contracted in the axial line direction.

One end of the variable shaft 120 is connected to the ultrasonic wave generating unit 30, and an opposite end of the variable shaft 120 is connected to the manipulation part 130 that will be described below. Accordingly, when the manipulation part 130 is moved in the vertical direction of the transducer 32, the ultrasonic wave generating unit 30 and the manipulation part 130 together may be moved in the vertical direction of the transducer 32.

The variable shaft 120 may include one or more shafts that have different diameters and that may be inserted and extracted in multiple steps.

The manipulation part 130 functions to move the variable shaft 120 in the vertical direction of the transducer 32. When the manipulation part 130 is moved in the vertical direction of the transducer 32, the ultrasonic wave generating unit 30 also is moved in the vertical direction of the transducer 32 in conjunction therewith whereby the focus depth of the ultrasonic waves of the transducer 32 may be easily adjusted.

As an example, the manipulation part 130 may be a driving means for driving the variable shaft 120 in the vertical direction of the transducer 32.

As another example, the manipulation part 130 may be a knob that is coupled to a distal end of the variable shaft 120. A force for moving the knob in the vertical direction of the transducer 32 may be applied to the knob by the user. Here, the manipulation part 130 may be moved along a rack gear having a specific length, in the vertical direction, on an outer surface of the cartridge housing 20. Furthermore, a latchet boss that is selectively stopped or released may be provided in the rack gear of the manipulation part 130.

In the embodiment, the variable shaft 120 is coupled to one surface of the connector 31 of the ultrasonic wave generating unit 30, and the movable shaft 40 is coupled to an opposite surface of the connector 31 of the ultrasonic wave generating unit 30.

In the embodiment, the movable shaft 40 is configured to be movable in the axial line direction of the variable shaft 120.

Accordingly, when the movable shaft 40 is moved in the axial line direction of the variable shaft 120, the ultrasonic wave generating unit 30 is moved together in the axial line direction of the variable shaft 120, and the variable shaft 120 is expanded and contracted in the axial line direction of the variable shaft 120.

Meanwhile, the connector 31 of the ultrasonic wave generating unit 30 and the movable shaft 40 may be coupled to each other to be separable through the third magnetic member 140 and the fourth magnetic member 150.

The third magnetic member 140 may be provided in the connector 31 of the ultrasonic wave generating unit 30 while facing the variable shaft 120. The third magnetic member 140 may have a length that is equal to or larger than a maximum movement distance of the variable shaft 120. Here, the maximum movement distance of the variable shaft 120 may be defined as a distance, by which the variable shaft 120 may be maximally moved from the cartridge housing 20 with respect to the vertical direction of the transducer 32.

The fourth magnetic member 150 may be provided in the movable shaft 40, and may be magnetically coupled to the third magnetic member 140. The fourth magnetic member 150 may have a length that is smaller than that of the third magnetic member 140 with respect to the vertical direction of the transducer 32.

As an example, the ultrasonic wave generating unit 30 may be moved in the vertical direction of the transducer 32 through a manipulation of the manipulation part 130, and may be moved in the axial line direction of the variable shaft 120 by the movable shaft after a target location in the vertical direction of the transducer 32 is determined.

Here, when the target location in the vertical direction of the transducer 32 for the ultrasonic wave generating unit 30 is determined, the focus depth of the ultrasonic waves of the transducer 32 may be adjusted to a target depth under skin.

Furthermore, while the ultrasonic wave generating unit 30 is moved in a linear path in the axial line direction of the variable shaft 120 by the movable shaft 40, the transducer 32 may be operated to provide the ultrasonic waves generated by the transducer 32 at the target depth under the skin along the linear path in the axial line direction of the variable shaft 120.

Meanwhile, an ultrasonic wave generating cartridge according to the inventive concept is attached to and detached from the handpiece 10, and may include the cartridge housing 20, the ultrasonic wave generating unit 30, the movable shaft 40, the guide part 50, and the elastic members 60.

Furthermore, the ultrasonic wave generating cartridge according to the inventive concept may further include the bushing 70, the first tube 80, and the second tube 90.

According to the inventive concept, the ultrasonic wave generating apparatus capable of adjusting a focus depth of ultrasonic waves according to an embodiment of the inventive concept may easily adjust the focus depth of the ultrasonic waves according to a target depth in skin.

Furthermore, according to the ultrasonic wave generating apparatus capable of adjusting a focus depth of ultrasonic waves according to an embodiment of the inventive concept, the ultrasonic wave generating unit may be prevented from being pivoted when the ultrasonic wave generating unit is moved in the vertical direction and the ultrasonic wave generating unit can smoothly maintain level at the focus depth because the pair of elastic members elastically support the guide shaft that is inserted into the ultrasonic wave generating unit.

The ultrasonic wave generating apparatus according to an embodiment of the inventive concept may easily adjust a focus depth of ultrasonic waves according to a target depth in skin.

Furthermore, according to the ultrasonic wave generating apparatus capable of adjusting a focus depth of ultrasonic waves according to an embodiment of the inventive concept, the ultrasonic wave generating unit may be prevented from being pivoted when the ultrasonic wave generating unit is moved in the vertical direction and the ultrasonic wave generating unit may be smoothly horizontally maintained at the focus depth because the pair of elastic members elastically support the guide shaft that is inserted into the ultrasonic wave generating unit.

The effects of the inventive concept are not limited to the above-mentioned ones, and the unmentioned effects will be clearly understood by an ordinary person in the art from the following description.

Although the embodiments of the inventive concept have been described with reference to the attached drawings until now, an ordinary person in the art, to which the inventive concept pertains, may understand that the inventive concept may be carried out in other detailed forms without changing the technical spirits or the essential features. Therefore, it should be understood that the above-described embodiments are exemplary in all aspects and are not restrictive.

What is claimed is:

1. An ultrasonic wave generating apparatus capable of adjusting a focus depth of ultrasonic waves, the ultrasonic wave generating apparatus comprising:
- a handpiece;
- a cartridge housing separably mounted on the handpiece;
- an ultrasonic wave generating unit in the cartridge housing and including a transducer configured to generate the ultrasonic waves;
- a movable shaft configured to be movable in an axial line direction and a vertical direction of the transducer; and
- a guide shaft in the cartridge housing, the guide shaft passing through the ultrasonic wave generating unit and configured to guide the ultrasonic wave generating unit such that the ultrasonic wave generating unit is movable in the vertical direction and the axial line direction.

2. The ultrasonic wave generating apparatus of claim 1, further comprising:
- one or more elastic members in the ultrasonic wave generating unit.

3. The ultrasonic wave generating apparatus of claim 2, wherein the elastic members face each other with the guide shaft interposed therebetween, and the elastic members are configured to elastically support the guide shaft.

4. The ultrasonic wave generating apparatus of claim 1, wherein the ultrasonic wave generating unit includes a mounter, to which the movable shaft is coupled to be separable,
- wherein a fixing hole is formed in any one of the movable shaft and the mounter, and
- wherein a fixing boss which is separably coupled to the fixing hole is formed on the other one of the movable shaft and the mounter.

5. The ultrasonic wave generating apparatus of claim 4, wherein a tapered portion, which has an inner diameter getting smaller in an insertion direction of the fixing boss, is formed on one side of the fixing hole, into which the fixing boss is inserted.

6. The ultrasonic wave generating apparatus of claim 5, further comprising:
- a first tube and a second tube formed on opposite sides of the mounter and configured to be expanded and contracted.

7. The ultrasonic wave generating apparatus of claim 5, further comprising:
- a first magnetic member in the fixing hole; and
- a second magnetic member in the fixing boss and magnetically coupled to the first magnetic member.

8. An ultrasonic wave generating apparatus capable of adjusting a focus depth of ultrasonic waves, the ultrasonic wave generating apparatus comprising:
- a handpiece;

a cartridge housing separably mounted on the handpiece;

an ultrasonic wave generating unit in the cartridge housing and including a transducer configured to generate the ultrasonic waves;

a variable shaft connected to the ultrasonic wave generating unit, configured to be movable in a vertical direction of the transducer, and configured to be expanded and contracted in an axial line direction thereof;

a guide shaft in the cartridge housing, the guide shaft passing through the ultrasonic wave generating unit and configured to guide the ultrasonic wave generating unit such that the ultrasonic wave generating unit is movable in the vertical direction and the axial line direction; and a manipulation part configured to move the variable shaft in the vertical direction.

9. The ultrasonic wave generating apparatus of claim 8, further comprising:

a movable shaft configured to be movable in the axial line direction of the variable shaft.

10. The ultrasonic wave generating apparatus of claim 8, further comprising:

one or more elastic members in the ultrasonic wave generating unit.

11. The ultrasonic wave generating apparatus of claim 10, wherein the elastic members face each other with the guide shaft interposed therebetween, and the elastic members are configured to elastically support the guide shaft.

12. The ultrasonic wave generating apparatus of claim 8, wherein the variable shaft includes:

one or more shafts having different diameters, and being inserted and extracted in multiple steps.

* * * * *